United States Patent
Kadoury et al.

(10) Patent No.: US 10,290,076 B2
(45) Date of Patent: May 14, 2019

(54) SYSTEM AND METHOD FOR AUTOMATED INITIALIZATION AND REGISTRATION OF NAVIGATION SYSTEM

(75) Inventors: Samuel Kadoury, Olney, MD (US);
Jochen Kruecker, Washington, DC (US); James Robertson Jago, Seattle, WA (US); Bradford Johns Wood, Potomac, MD (US); Antoine Collet-Billon, Paris (FR); Cecile Dufour, Paris (FR)

(73) Assignees: The United States of America, as represented by the Secretary, Department of Health and Human Services, Washington, DC (US); Koninklijke Philips N.V., Eindhoven (NL)

( * ) Notice: Subject to any disclaimer, the term of this patent is extended or adjusted under 35 U.S.C. 154(b) by 632 days.

(21) Appl. No.: 14/002,132

(22) PCT Filed: Mar. 2, 2012

(86) PCT No.: PCT/IB2012/050999
§ 371 (c)(1),
(2), (4) Date: Feb. 26, 2014

(87) PCT Pub. No.: WO2012/117381
PCT Pub. Date: Sep. 7, 2012

(65) Prior Publication Data
US 2014/0193053 A1    Jul. 10, 2014

Related U.S. Application Data (60) Provisional application No. 61/448,714, filed on Mar. 3, 2011.

(51) Int. Cl.
*G06K 9/00* (2006.01)
*G06T 3/00* (2006.01)
(Continued)

(52) U.S. Cl.
CPC ............ *G06T 3/0068* (2013.01); *A61B 90/36* (2016.02); *G06T 11/008* (2013.01); *G06T 15/08* (2013.01);
(Continued)

(58) Field of Classification Search
CPC ............ A61B 19/52; A61B 2019/5246; A61B 2019/5276; A61B 2019/5291;
(Continued)

(56) References Cited

U.S. PATENT DOCUMENTS

| 6,203,497 | B1 | 3/2001 | Dekel et al. |
| 2009/0097778 | A1 | 4/2009 | Washburn et al. |

(Continued)

FOREIGN PATENT DOCUMENTS

| CN | 1985773 A | 6/2007 |
| CN | 101170961 A | 4/2008 |

(Continued)

OTHER PUBLICATIONS

Krücker, Jochen, et al. "Fusion of real-time transrectal ultrasound with preacquired MRI for multimodality prostate imaging." Medical Imaging. International Society for Optics and Photonics, 2007.*

(Continued)

*Primary Examiner* — Nirav G Patel (57) ABSTRACT

A system and method for image registration includes tracking (508) a scanner probe in a position along a skin surface of a patient. Image planes corresponding to the position are acquired (510). A three-dimensional volume of a region of interest is reconstructed (512) from the image planes. A search of an image volume is initialized (514) to determine candidate images to register the image volume with the three-dimensional volume by employing pose information of the scanner probe during image plane acquisition, and physical constraints of a pose of the scanner probe. The (Continued)

image volume is registered (522) with the three-dimensional volume.

17 Claims, 6 Drawing Sheets

(51) Int. Cl.
- *G06T 11/00* (2006.01)
- *G06T 15/08* (2011.01)
- *A61B 90/00* (2016.01)
- *A61B 34/20* (2016.01)
- *A61B 8/08* (2006.01)

(52) U.S. Cl.
CPC ..... *A61B 8/5261* (2013.01); *A61B 2034/2046* (2016.02); *A61B 2090/365* (2016.02); *A61B 2090/367* (2016.02); *A61B 2090/378* (2016.02)

(58) Field of Classification Search
CPC .......... A61B 2019/5295; G06T 11/008; G06T 15/08; G06T 3/0068
See application file for complete search history.

(56) References Cited

U.S. PATENT DOCUMENTS

| | | |
|---|---|---|
| 2009/0326373 A1 | 12/2009 | Boese et al. |
| 2010/0286517 A1 | 11/2010 | Kamen et al. |
| 2011/0082459 A1* | 4/2011 | Aravot ............... A61B 17/14 606/79 |

FOREIGN PATENT DOCUMENTS

| | | |
|---|---|---|
| EP | 1720039 | 11/2006 |
| WO | WO2006089426 | 8/2006 |

OTHER PUBLICATIONS

Guerrero, Julian, et al. "Real-time vessel segmentation and tracking for ultrasound imaging applications." Medical Imaging, IEEE Transactions on 26.8 (2007): 1079-1090.*

Hill, Derek LG, et al. "Medical image registration." Physics in medicine and biology 46.3 (2001): R1.*

King, A. P., et al. "Tracking liver motion using 3-D ultrasound and a surface based statistical shape model." Mathematical Methods in Biomedical Image Analysis, 2001. MMBIA 2001. IEEE Workshop on. IEEE, 2001.*

Hughes, S. W., et al. "Volume estimation from multiplanar 2D ultrasound images using a remote electromagnetic position and orientation sensor." Ultrasound in medicine & biology 22.5 (1996): 561-572.*

* cited by examiner

SYSTEM AND METHOD FOR AUTOMATED INITIALIZATION AND REGISTRATION OF NAVIGATION SYSTEM

This application is the U.S. National Phase application under 35 U.S.C. § 371 of International Application Serial No. PCT/IB2012/050999, filed on Mar. 2, 2012, which claims the benefit of U.S. Application Ser. No. 61/448,714, filed on Mar. 3, 2011. These applications are hereby incorporated by reference herein.

GOVERNMENT RIGHTS

This invention was made in the performance of a Cooperative Research and Development Agreement with the United States Public Health Service (CRADA No. NCI-NIHCC-01864). The Government of the United States has certain rights in the invention.

This disclosure relates to medical systems and more particularly to systems and methods for device navigation using coordinated registration between different imaging modalities.

Surgery and minimally invasive therapy require reliable, precise navigation along predefined paths to predetermined target points. Many kinds of interventions are guided based on pre-procedural high-resolution three-dimensional (3D) images taken from a region of interest. Typically, a computed tomography (CT) or magnetic resonance (MR) scanner acquires images before an intervention (pre-operative images). These modalities are not real-time, at least when high resolution is required and their use for imaging during an intervention is thus very limited. Proper spatial registration of pre-operative images in combination with a navigation system would make images much more effective during an interventional procedure.

Attaching fiducial markers to a patient's skin before taking a high-resolution 3D image is one widely used method to facilitate spatial registration. These markers can easily be localized in the image, i.e., their spatial coordinates in an image coordinate system can be determined precisely. To perform the actual intervention, the patient is placed on the intervention table. The positions of the fiducial markers in the coordinate system of the position measurement system are obtained by touching the markers with a spatially tracked pointer device. By mapping these coordinates to the coordinates of the markers localized in the image, it is possible to determine a transformation from a position measurement system coordinates to image coordinates. Provided a fixed spatial relationship between the patient and the measurement system exists, it is then possible to determine the position of a tracked device in the pre-operative image.

Typically, a physician uses a live-imaging modality, like ultrasound, during the procedure to gain additional information but also as a verification of the registration to enhance reliability when using the pre-operative image information. The position of this live imaging modality is tracked as well, so the spatial coordinates of the live image in the tracking coordinate system are known.

Fiducial markers, however, cannot be used in a number of situations. These include: 1) When trying to navigate on pre-procedural diagnostic images that were obtained before fiducials could be attached, and that cannot be repeated with fiducials attached (e.g., because of concerns about cost, radiation dose or contrast medium exposure, workflow, etc.). 2) When the field of view of the imaging modality is limited such that field of view cannot cover both the skin fiducials and the region of interest for the intervention.

When fiducial markers are unavailable for registration, alternative means must be used to match the pre-procedural image space to the navigation system space. Currently available methods are limited to manual registration using point pair matching (e.g., finding corresponding anatomical landmarks in the live intra-procedural modality such as ultrasound, and in the pre-procedural image); scan plane matching (choosing a "live" image plane in the region of interest, and adjusting the registration transformation to map it to a corresponding image plane in the pre-procedural image, or vice versa, selecting an image plane in the pre-procedural image, and adjusting the "live" image plane to match the pre-procedural image plane) or a combination of these.

Organ motion and deformation between the pre-procedural image acquisition and the interventional procedure, as well as the difficulty in reliably identifying equivalent targets in images having very different characteristics (such as Ultrasound versus CT/MR), turn this manual registration process into a difficult task, often taking significant amounts of time, and/or leading to inaccurate registration results.

It is quite challenging to determine an accurate and reliable transfer function to map image pixels from one modality to another given the inherently different image formation phenomena, as well as changing contrast and intensity levels. Respiratory phases and varying elastic deformation of the structure of interest also have an important role in determining accurate registration. Various approaches have been described including various image-based approaches to establish suitable similarity measures between US and CT or MR. However, reliable automatic segmentation of a particular structure becomes one of the main sources of error which can hinder the quality of the registration. Such methods remain highly supervised since they require either a manual initialization of the registration transformation or manual gating of the ultrasound frames acquired for registration purposes.

In accordance with the present principles, systems and methods are provided which create reliable registration initialization for automatic fusion of pre-operative images to intra-operative images without relying on manual alignment or selection of processing intra-operative frames. The present embodiments include subject-specific structure shape information (e.g., a reference organ or boundary) obtained from intra-operative images to provide proper alignment with a corresponding pre-operative shape model. The present embodiments provide useful information on an effective search space in terms of translation and rotation parameters, as well as a starting point for an automatic image-based registration approach.

An integrated framework provides an accurate and real-time updated transformation chain to connect free-hand two-dimensional (2D) ultrasound (US) images to a pre-acquired 3D reference volume from another modality. Based on this framework, an initialization of a registration matrix is obtained which links the pre-operative coordinate system with an intra-operative electromagnetic reference using 3D surface shapes acquired in tracking space. The present methods are able to first estimate an approximate registration matrix by determining the main orientation using the tracking information from a probe position taken near the patient's midline, followed by a translation adjustment which aligns recorded probe positions to a patient's skin segmentation. This avoids using US image features which may be subject to poor image quality. Once the main parameters are estimated, a patient-specific US surface model from a 3D reconstructed volume is obtained using a restricted confidence-based region growing method. The obtained accurate and subject-specific initialization can lead to better registration performance as compared with existing fiducial marker registration methods.

In accordance with the present principles, a system and method for image registration includes tracking a scanner probe in a position along a skin surface of a patient. Image planes corresponding to the position are acquired. A three-dimensional volume of a region of interest is reconstructed from the image planes. A search of an image volume is initialized to determine candidate images to register the image volume with the three-dimensional volume by employing pose information of the scanner probe during image plane acquisition, and physical constraints of a pose of the scanner probe. The image volume is registered with the three-dimensional volume.

In another embodiment, a system and method for image registration includes segmenting a reference organ and a skin surface image of a patient in an image volume; tracking a scanner probe in at least one position along the skin surface of a patient; acquiring images corresponding to the at least one position and the reference organ; reconstructing a three-dimensional volume of the reference organ from the image planes; initializing a transformation matrix with initial parameter values constrained by poses and physical constraints of the scanner probe during image acquisition to determine the transformation matrix between the image volume with the three-dimensional volume; and optimizing the transformation matrix to find coordinates that register the image volume with the three-dimensional volume using a cost function.

A system for image registration includes a spatial trackable scanner probe, an imaging device configured to acquire image planes corresponding to at least one position of the scanner probe; and an image processing module. The image processing module is configured to reconstruct a three-dimensional volume of a region of interest from the image planes. The image processing module is further configured to initialize a search of a stored model of the image volume to determine candidate images to register the image volume with the three-dimensional volume by employing pose information of the scanner probe during image plane acquisition, and physical constraints of the pose of the scanner probe. A registration module is configured to register the image volume with the three-dimensional volume.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Medical navigation systems require a registration procedure to align the coordinate systems of the navigation system and a patient. Fiducial markers attached to the patient permit semi-automatic or fully automatic registration if a roadmap image including the fiducial markers can be obtained. In many cases however, use of fiducial markers is not feasible, necessitating a potentially time consuming and inaccurate manual registration procedure. The present principles provide a system and method for rapid and accurate automatic or semi-automatic registration. In particularly useful embodiments, a prescribed set of image acquisitions are combined in standard imaging planes with subsequent image processing of pre-procedure and intra-procedure imaging.

The present embodiments provide a system and method to automatically obtain a reliable subject-specific initialization for registration of internal organs, such as, e.g., a liver, from ultrasound (US) images to a prior pre-operative image volumes (e.g., CT or MR) during interventional or diagnostic procedures. Automatic multimodal image registration is challenging, since the final registration performance depends on the image quality from both reference and target modalities, segmentation accuracy and reliable starting point for optimizing the transformation.

Existing methods rely either on manually identified fiducials which can correlate ultrasound with CT/MR or use image-based features to automatically register modalities. However, these systems require a manual initialization which can easily lead to suboptimal solutions. The present embodiments address these problems by using a framework which exploits tracked intra-operative images (e.g., US) as a multiplanar registration (MPR) selector integrated with an image-based segmentation method, which can accurately transform the obtained free-hand 2D image to a pre-acquired 3D reference volume of another modality. Based on this framework, an initialization of the rigid transformation matrix is obtained independently of image quality, and is subsequently refined via a constrained shape-matching approach from a segmented organ boundary.

The improved registration results have several applications. These applications may include at least some of: (1) Verification/monitoring of current fiducial-based registration accuracy between electromagnetic (EM) tracked ultrasonic (US) images and a pre-acquired 3D image; (2) Estimation of tumor or target locations on pre-operative images; (3) Improved initialization for image-based registration of 2D ultrasound and pre-acquired 3D images; (4) Non-rigid (elastic) correction to registration of 2D ultrasound and pre-acquired 3D images; and (5) Verification of tumor existence and assessment in a diagnostic setting.

It should be understood that the present embodiments will be described in terms of registering a pre-operative image volume with an intra-operative three-dimensional volume; however, the systems and methods in accordance with the present principles can be applied to registrations between any of pre-operative, intra-operative, and post-operative images for monitoring, interventional procedures and/or diagnostic applications.

It also should be understood that the present invention will be described in terms of medical systems and instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements. The present principles may be applied for guidance of many interventional or surgical procedures that need registration of the patient with a prior medical image (e.g., biopsy, ablation, embolization, drainage, etc.). These principles may also be applied in diagnostic applications that employ multi-modality registration and may not involve interventional procedures. For example, since ultrasound and CT provide complimentary diagnostic information, it may be beneficial to register these two modalities to ensure that the same lesion is being evaluated in both images. For these non-interventional applications, it should also be clear that the multi-modality registration step, although utilizing tracking and imaging information acquired during the ultrasound exam, may actually be performed either during the ultrasound imaging exam or retrospectively, for example on an imaging workstation after the exam is completed. The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 1:
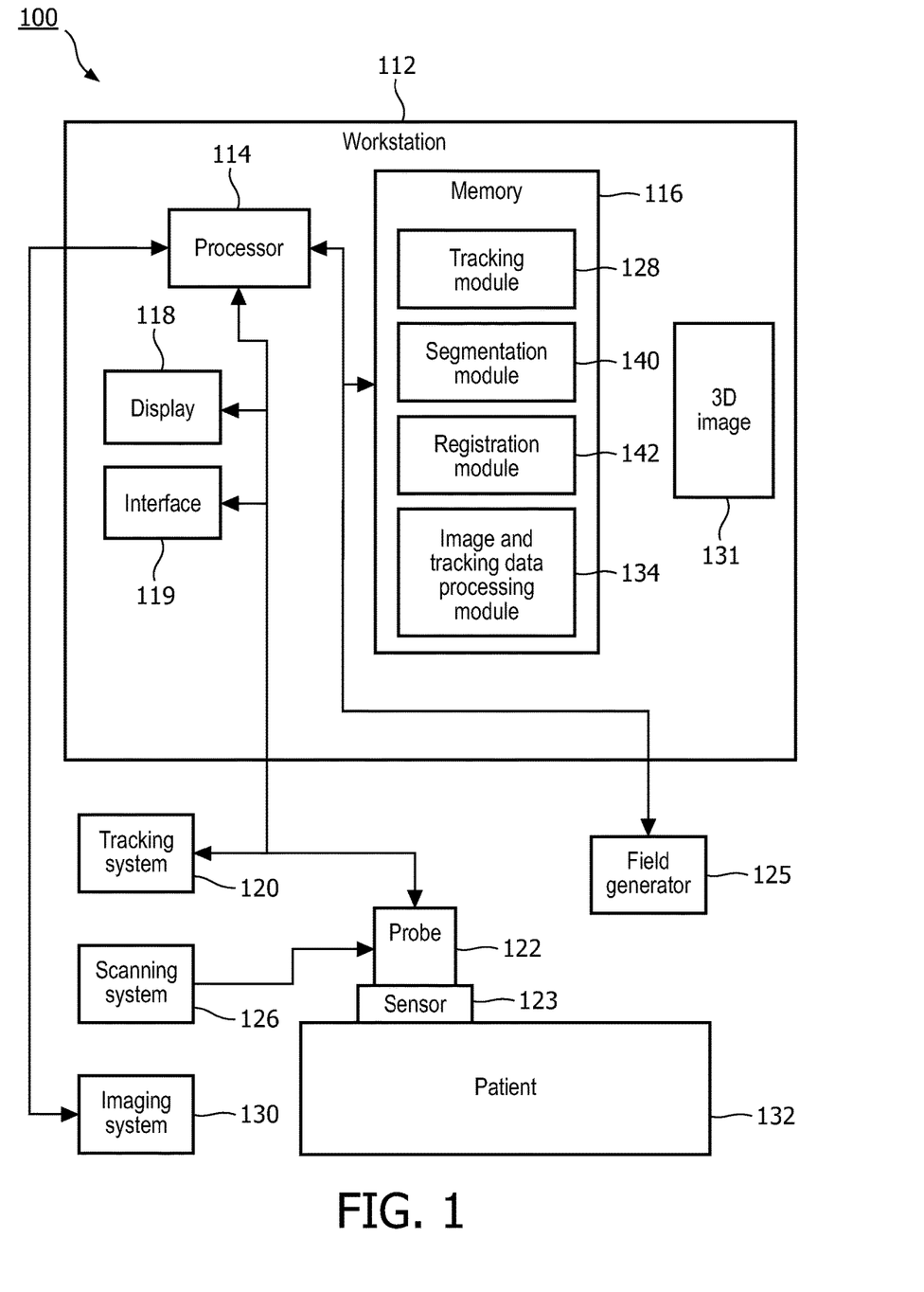
FIG. 1 is a block/flow diagram showing a system/method for image registration in accordance with the present principles.

Referring now to the drawings in which like numerals represent the same or similar elements and initially to FIG. 1, a system 100 for performing a medical procedure is illustratively depicted. System 100 may include a workstation or console 112 from which a procedure is supervised and managed. Workstation 112 preferably includes one or more processors 114 and memory 116 for storing programs and applications. Memory 116 may store one or more program modules employed in initializing and providing registration of images and tracking systems.

System 100 includes a position tracking system 120. The workstation 112 is connected to the tracking system 120 and a scanning device 126. The workstation 112 obtains images from the scanner 126, and concurrently obtains corresponding position information from a sensor 123. The workstation 112 may also be integrated in and become part of the scanner 126 or vice versa.

The position tracking system 120 may include an electromagnetic (EM), optical or other tracking technology and is employed to spatially track a real-time probe 122 of the scanning device 126. The tracking system 120 may work with a tracking module 128 in memory 116 of workstation 112 for correlating probe positions with images as will be explained in greater detail herein. The probe 122 includes the sensor or sensors 123 employed by the tracking system 120. In a case where the sensor 123 includes an EM sensor, a tracking field generator 125 may be employed to create a magnetic field to enable EM tracking for the tracking system 120. The field generator 125 may be placed near the patient 132 during a medical procedure. In one embodiment, the tracking sensor 123 is attached to the probe or ultrasound transducer.

The scanning device 126 may include an ultrasonic (US) scanning device, although other real-time imaging system may be employed. For ease of explanation, the scanning device 126 will illustratively be described in terms of ultrasonic technology. Images gathered in real-time during a procedure will be referred to as intra-operative images.

An imaging system 130 may be available in system 100 but need not be. Imaging system 130 may be provided for collecting pre-operative imaging data or real-time intra-operative imaging data. The pre-operative imaging may be performed at another facility, location, etc. in advance of any procedure. These 3D images 131 may be stored in memory 116.

The imaging system 130 provides a pre-acquired medical image or volume of a patient or subject 132. These images will be referred to as pre-operative images. The imaging system may include a computed tomography (CT) system, a magnetic resonance imaging (MRI) system, a pre-operative 3D US imaging system, or other imaging systems.

The memory 116 of workstation 112 includes an image and tracking data processing module 134, which is configured to process images as well as data from the tracking system 120. The processing module 134 performs a workflow which includes tracking one or several ultrasound probe poses (e.g., for axial midline images) with the ultrasound probe 122 from the scanner 126 at arbitrary positions, perpendicular to a skin surface of the subject 132. The processing module 134 further acquires additional image planes in an area of interest, for reconstruction into a three-dimensional (3D) US volume from scanner 126.

The processing module 134 automatically initializes an intra-operative to pre-operative image registration search (e.g., US-CT) space, utilizing knowledge of an approximate pose of the ultrasound probe 122 (from tracking data) during an image plane acquisition, and utilizing physical constraints of the ultrasound probe 122 pose during the image plane and volumetric acquisition, e.g., the ultrasound probe 122 needs to be in contact with the patient's skin for imaging.

The processing module 134 further provides intra-operative to pre-operative image registration optimization. The optimization is preferably based on image processing of the pre-operative medical image and the intra-operative (US) images, including automated segmentation of anatomical structures. A similarity measure is defined between the pre-operative images and the intra-operative images. Using known optimization techniques such as exhaustive search, or Downhill Simplex, the similarity measure is optimized to identify a best match between images.

In one embodiment, a clinical workflow records tracking data from the probe 122 at two locations (e.g., near a sternum of the patient 132) and tracking data from a location acquired during an ultrasonic liver or other organ/boundary sweep. The liver is employed in this embodiment as a reference due to its distinctive shape. Other organs or references may be employed.

A segmentation module 140 segments images of organs using segmentation methods. The segmentation module 140 acquires and stores pre-operative 3D volumes and uses them for 3D segmentation of a skin surface represented by a cloud of 3D coordinate points. An alignment or registration module 142 uses the cloud of coordinates for initial alignment and for constraining an optimization search space. The 3D segmentation of the liver shape (or other organ shapes) represented by a triangulated mesh model may be employed for a model-based registration approach.

In this embodiment, the processing module acquires and processes tracking sensor 123 coordinates in real-time, and employs them for computing an automatic image-based rigid transformation matrix between a pre-acquired 3D shape model of the liver and a segmented liver surface obtained from an intra-operative 3D US volume. A multiplanar registration (MPR) determined by the tracking sensor 123 shows corresponding pre-operative image information (from, e.g., CT or MR) at a latest acquired real-time image with liver boundary (from real-time intra-operative US image) fitting to an edge of the pre-operative image liver segmentation.

In another embodiment, the workstation enables accurate multimodal registration by acquiring and processing tracking sensor 123 coordinates in real-time. The sensor 123 coordinates are employed for 3D patient-specific segmentation (e.g., of US images) in segmentation module 142 of a liver or other boundary using a confidence-based region growing which propagates through a volume. This process collects voxels which belong to an intensity interval with a dynamically adjustable standard deviation. This enables the creation of a binary volume of a surface, e.g., a liver surface. A mask is subsequently processed to extract a surface representation of a liver capsule and boundary. The resulting segmentation is employed for optimizing image alignment between modalities. The parameter search space is restricted or constrained by an area defined by a skin surface segmentation which penalizes probe transformations mapping away from the skin, such that the MPR determined by the tracking sensor shows corresponding pre-operative image information (e.g., from CT or MR) at a latest acquired real-time image with the US liver boundary fitting to the edge of the pre-operative liver segmentation.

Workstation 112 may include a display 118 for viewing internal images of a subject. Display 118 may also permit a user to interact with the workstation 112 and its components and functions. This is further facilitated by an interface 119 which may include a keyboard, mouse, a joystick or any other peripheral or control to permit user interaction with the workstation 112. The user interface 119 guides the user through the workflow, prompts for and guides initiation of individual work steps, and permits interactive correction to any automatically computed registrations.

In one embodiment, the interface 119 and display 118 permit the user to receive instructions or prompts through the work station 112 to assist the use through each stage of the registration process utilizing text, diagrams or both. The interface 119 may provide manual controls or overrides to control the image registration and initialization process as described in greater detail below by translating/rotating the intra-operative image and pre-operative volumes relative to one another. The interface 119 and display 118 permit the user to start the optimization process from any manually adjusted starting pose. In addition, a user may be prompted through the interface 119 and display 118 to select from a choice of similarity measures, optimized for the specific image acquisition in the given patient. The display 118 permits visualization, in one or several cut-planes or in 3D renderings, with or without superimposition of segmentation information, the intra-operative/pre-operative (e.g., US-CT) alignment at any stage. The interface 119 enables a user to accept or reject any registration result.

Figure 2:
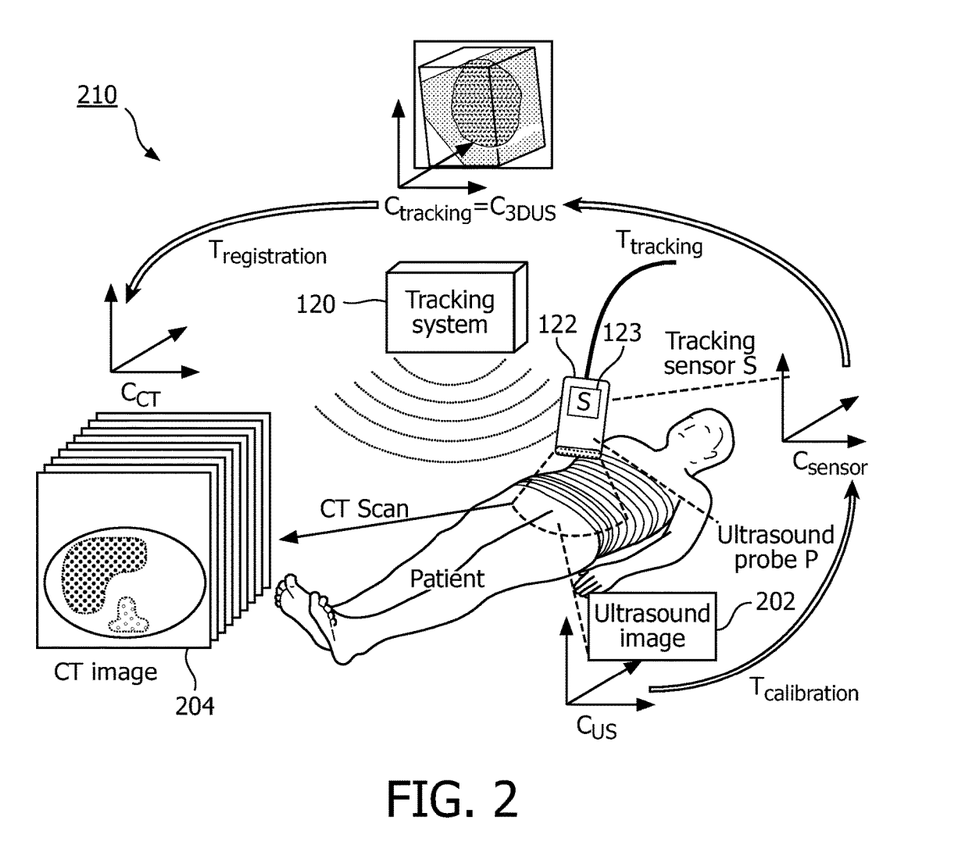
FIG. 2 is a schematic diagram showing a chain of transformations employed in registration of images in accordance with the present principles.

Referring to FIG. 2, further details for image registration are provided by illustratively showing coordinate transformations for registration of different modalities in accordance with the present principles. In one example, a chain of transformations 210 are employed to fuse a live ultrasound image 202 (acquired by the probe 122 tracked with tracking sensor 123) with a pre-acquired CT image 204. A one-time calibration procedure determines a transformation $T_{calibration}$, which relates a coordinate system $C_{US}$ of the real-time ultrasound image to a coordinate system $C_{sensor}$ of the tracking sensor 123 attached to the probe 122. The real-time tracking information from the tracking system 120 provides the transformation $T_{tracking}$, which relates a coordinate system $C_{sensor}$ to a coordinate system $C_{tracking}$ of the tracking system 120 (e.g., from the electromagnetic field generator 125). The transformation $T_{registration}$ is initially unknown and needs to be established.

$T_{registration}$ relates the coordinate system of the tracking system $C_{tracking}$ to a coordinate system $C_{CT}$ of the CT image. Once established, any pixel in the real-time ultrasound image 202 can be related to a voxel in the CT image 204 via the transformation chain 210, which permits side-by-side display, fusion, etc. of corresponding US and CT image planes.

$T_{registration}$ is established by first reconstructing a 3D US volume from tracked 2D ultrasound images 202 in the coordinate system $C_{tracking}$ of the tracking system 120. Alternatively, the 3D US volume may be obtained using a 3D capable transducer without the need for tracked 2D planes. Such 3D capable transducers include transducers which acquire a 3D volume by mechanically sweeping a 1D imaging array through an arc (known as mechanical 3D transducers), and transducers which acquire a 3D volume by electronic steering of an ultrasound beam (known as 2D array or Matrix transducers). A subsequent image-based registration, determined by the optimal alignment of the 3D US with the CT image 204, provides a $T_{registration}$ that can then be used in the transformation chain 210 for processing of the real-time ultrasound image 202.

The image-based registration of the 3D US image 202 with the CT image 204 is needed but no known methods exist, save the present principles, to provide this registration in a robust, accurate and quick manner for any interventional or diagnostic setting.

Figure 3:
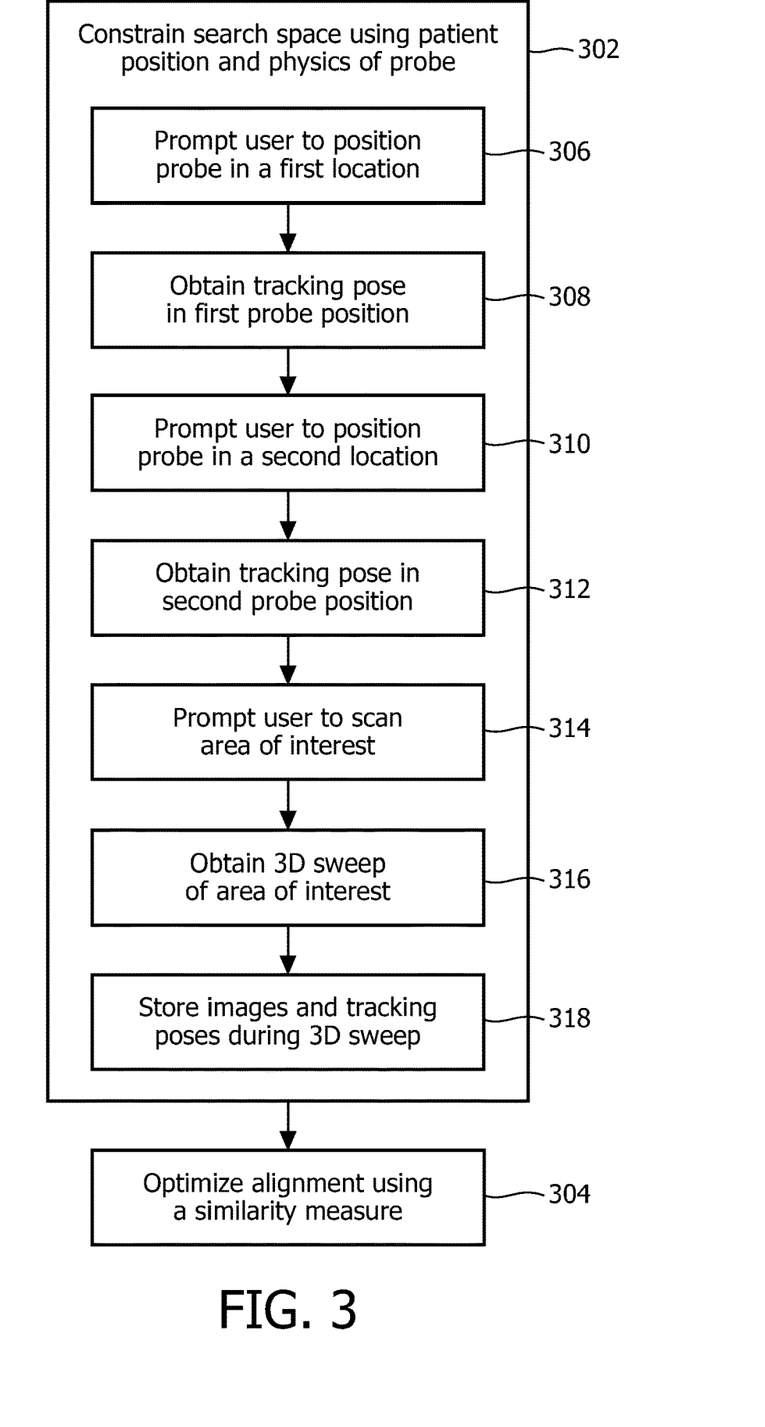
FIG. 3 is a block/flow diagram showing a system/method for enabling image registration in accordance with one illustrative embodiment.

Referring to FIG. 3, the registration ($T_{registration}$) may be completed in two parts. In block 302, a search space is constrained based on patient positioning and physics of ultrasound imaging for potential alignments (i.e., $T_{registration}$) of the 3D US with the CT. In block 304, a pre-segmentation on the CT scan is performed, and an appropriate similarity measure is defined between the 3D US and the segmented CT to optimize the alignment within the constrained search space.

The unconstrained search space for rigid registration comprises six degrees of freedom (e.g., 3 rotate, 3 translate). The search space can be effectively constrained by implementing a workflow and subsequent image processing that determine the approximate positioning of the patient relative to the tracking system (120), and by assuming that all ultrasound images are obtained while the ultrasound probe is in contact with the patient's skin.

In block 306, the workflow includes prompting a user to position the probe at any location near the midline of a sternum, as if to acquire an axial ultrasound plane midline on the patient, with the probe pointing exactly in the A-P (anterior-posterior) direction. In block 308, a tracking pose is obtained for the ultrasound probe (122) in this position. In block 310, the user is prompted to place the ultrasound probe at a second location (this is optional if other orientation mechanisms are employed) closer toward a lower portion (e.g., toward the legs or feet) (while maintaining probe angle). In block 312, the tracking pose is again obtained if the second position is employed.

In block 314, the user may be prompted to set the ultrasound scanner to a largest depth setting (e.g., 16, 20, 24 cm) that permits meaningful image acquisition in the area of interest in the patient (e.g., the largest depth setting before electronic noise obscures any image information in the deepest part of the image) and captures as much of the outer boundaries of the structure of interest as possible. Then, in block 316, the user is prompted to obtain a free-hand, mechanical, or electronic 3D sweep of the organ of interest with this depth setting.

In block 318, images and tracking poses are recorded during the sweep, and the acquired images are reconstructed into a 3D US volume. If supported by the ultrasound transducer, the 3D sweep may also be acquired by motorized or electronic means so that the 3D US volume is obtained automatically.

Figure 4:
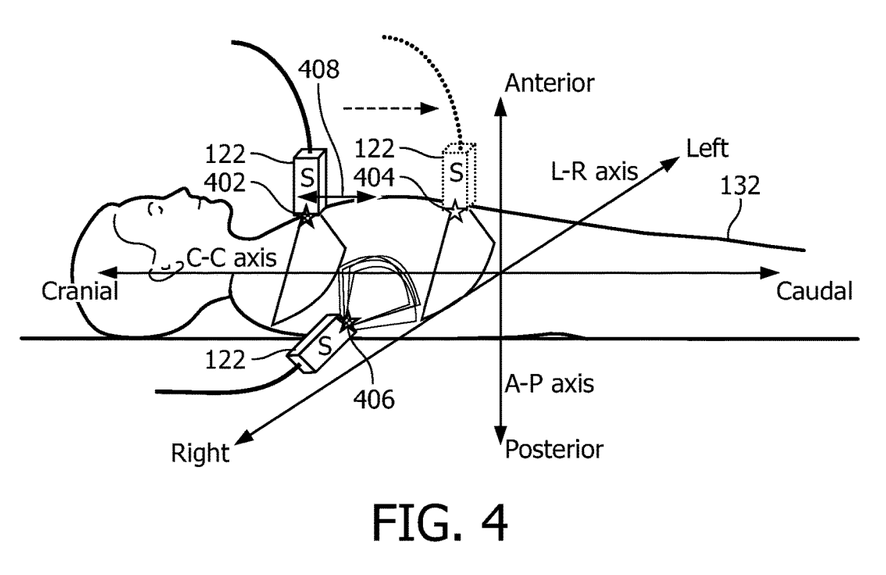
FIG. 4 is a schematic diagram showing an illustrative workflow for registering images in accordance with one illustrative embodiment.

Referring to FIG. 4 with continued reference to FIG. 3, transducer probe 122 locations 402 and 404 along midline and coordinate axes relative to the patient are illustratively shown. Block 310 determines the approximate rotational alignment (3 DOFs) between the tracking system space and the CT space. Block 314 resolves the ambiguity with regards to the patient's general orientation with respect to the tracking system or CT space, by determining an orientation and direction of the cranio-caudal (C-C) axis through a patient 132. Note that no ultrasound image is needed or utilized for either of the steps in blocks 310 and 314, the relevant information is derived from the tracked pose of a transducer (probe) 122 at positions 402 and 404. Both blocks 310 and 314 also determine the approximate lateral alignment (1 translational DOF) of the patient 132, by assuming the probe was positioned along a midline (L-R axis). One additional translational DOF (A-P axis alignment (Anterior to Posterior)) is determined by assuming the probe 122 was placed on the patient's skin. The skin surface can be easily extracted from the CT image ahead of time, the central midline L-R (left-right) axis can be extracted from the skin segmentations, and the A-P alignment is adjusted to map the physical probe surface during all the acquisition steps onto the skin surface.

It should be understood that while the acquisition of two or more positions is one useful implementation, e.g., to resolve the cranio-caudal direction ambiguity, other implementations may be employed. E.g., if the tracked ultrasound probe 122 is equipped with a direction marker 408 that clearly indicates how the probe should be oriented (e.g., which side is facing the head versus the feet of a patient), then the acquisition of six degrees of freedom tracking in just one such reference pose at the patient's midline is sufficient.

The remaining single unknown degree of freedom (DOF) is the translation along a cranio-caudal (C-C) axis. This translation can be approximately initialized by mapping a probe position (between positions 402 and 404 or using an orientation measure or marker 408 (e.g., probe orientation)) during a sweep acquisition to the center of the pre-segmented organ of interest in the CT, and/or by mapping the C-C axis probe position during block 310 to the pre-segmented sternum of the patient in the CT, and/or by placing the transducer probe at the position of the umbilicus in block 314 and similarly mapping this to the plane of the umbilicus in the CT.

Alignment optimization in block 304 of FIG. 3 is described in greater detail. With the registration transformation initialized in block 302, the transformation needs to be optimized by maximizing an appropriate similarity measure between the 3D US and the CT, in the vicinity of the initial pose. In the context of fusing pre-operative CT images of an abdominal target (e.g., liver, kidney, prostate, or other organ) with live US images, one similarity measure may utilize a pre-segmentation of a target organ surface from CT, spatially-dependent thresholding of high-intensity pixels in the ultrasound image (likely corresponding to the surface organ at a particular distance from the probe), and minimizing a weighted sum of squared distance between thresholded ultrasound pixels and the CT organ surface.

In another embodiment, a similarity measure may utilize a pre-segmentation of the target organ surface from CT, and maximize the average ultrasound pixel values that map onto the CT target organ surface. Another similarity measure for a target organ of interest may utilize a pre-segmentation of CT liver vessels, and minimize the average ultrasound pixel values that map onto the CT liver vessels. Another embodiment includes the alignment with a segmentation of US liver vessels maximized. A similarity measure may utilize a pre-segmentation of the target organ surface from CT, and minimize a pointset-to-pointset measure that maps a cloud of points created from ultrasound to the CT organ surface. The similarity measure may also include a weighted combination of any subset of the above or other similarity measures.

In another embodiment, the registration processing is performed on one organ, which is not the same as the organ on which the clinical procedure is performed. For example, the registration can be performed on the liver, but the clinical procedure targets a kidney.

In addition, tracking data is recorded from a location 406 acquired during an ultrasonic liver (or other organ or feature) sweep. As described, pre-operative images are acquired and stored, e.g., 3D CT or MR volumes. These pre-operative images are subjected to 3D segmentation of a skin surface represented by a cloud of 3D coordinate points. The skin segmentation is employed for an initial alignment and for constraining the optimization search space. A 3D segmentation of a liver shape (or other distinctive shaped organ) may be represented by a triangulated mesh model. The liver shape is employed for a model-based registration approach.

During a procedure, a sensor (123) has its coordinates acquired and processed in real-time as a transducer probe 122 is positioned at positions 402 and 404. The tracked sensor coordinates are employed to compute an automatic image-based rigid transformation matrix between of the 3D shape model of the liver and a segmented liver surface obtained from an intra-operative 3D US volume taken at position 406. Registration is determined between the pre-operative image information (from CT, MR) for a latest acquired real-time image (intra-operative) by aligning a liver boundary to the segmented liver image.

Another method for enabling accurate multimodal registration includes acquiring and processing tracking sensor coordinates in real-time, and providing 3D US patient-specific segmentation of the liver boundary using a confidence-based region growing which propagates through the volume. This process collects voxels which belong to an intensity interval with a dynamically adjustable standard deviation to enable the creation of a binary volume of the liver surface or a mask. The mask is subsequently processed to extract a surface representation of the liver capsule and boundary. The resulting segmentation may be employed for optimizing the image alignment between modalities.

A parameter search space is restricted by the area defined by a skin surface segmentation which penalizes probe transformations mapping away from the skin. Registration is determined between the pre-operative image information (from CT, MR) for a latest acquired real-time image (intra-operative) by aligning a liver boundary to the segmented liver image.

Figure 5:
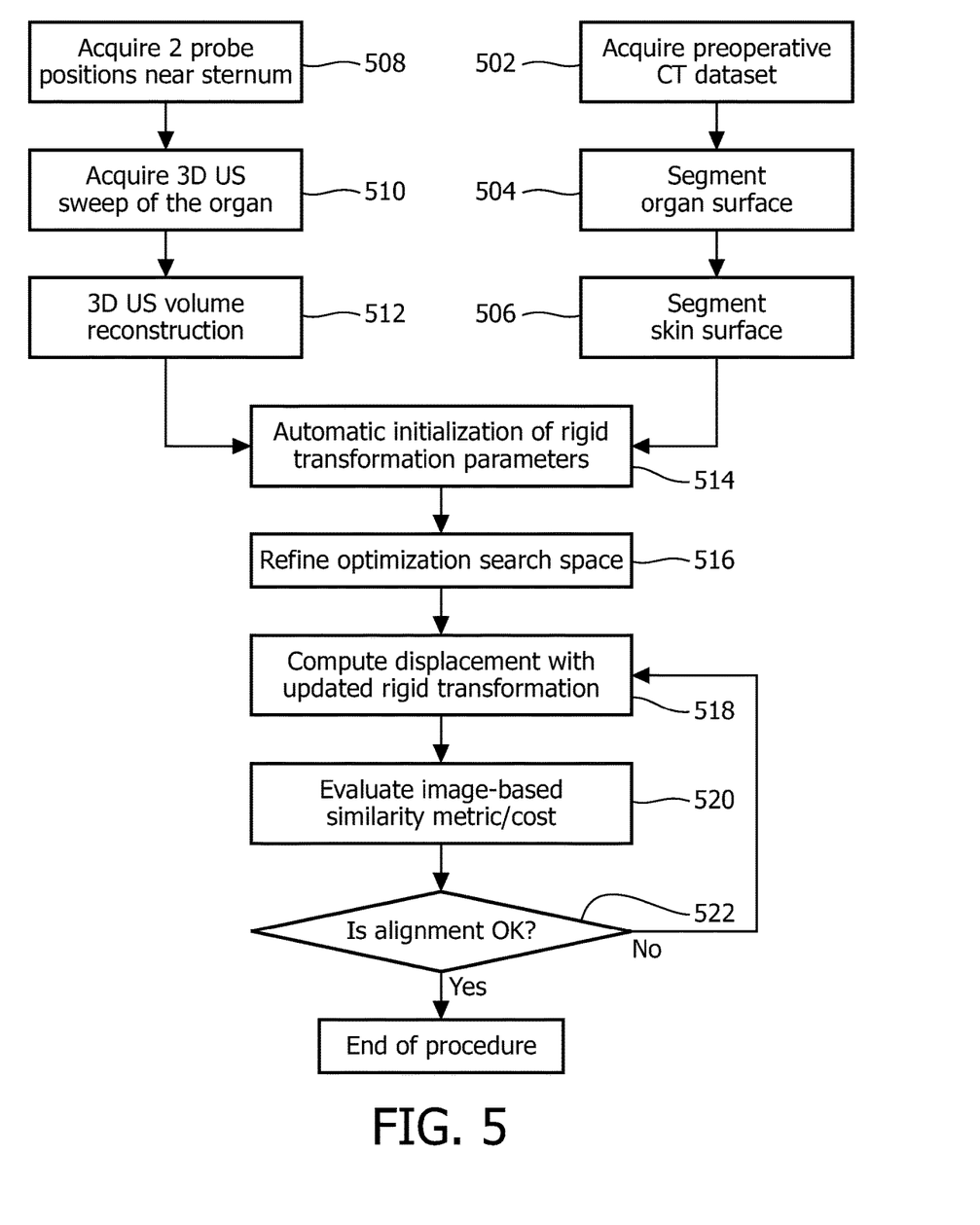
FIG. 5 is a block/flow diagram showing a system/method for performing image registration in accordance with one embodiment.

Referring to FIG. 5, an exemplary method for aligning images is illustratively shown. In block 502, pre-operative images (e.g., CT images) are collected and stored. In block 504, an organ surface is segmented by known methods. In block 506, a skin surface is segmented. In block 508, two probe positions are determined, e.g., near a sternum or other biological reference. In block 510, 3D sweeps (e.g., US scans) of an organ of interest are performed. In block 512, a 3D volume reconstruction of the 3D sweeps is performed.

In block 514, automatic initialization of rigid transformation parameters is performed. This includes computing transformation matrices and registering coordinate systems. In block 516, an optimization search space is refined by restricting degrees of freedom in images (or data). In block 518, updated rigid transformations are computed. In block 520, an image-based similarity metric is selected and evaluated. In block 522, alignment between images is checked. If the alignment is satisfactory, the process is ended. If the alignment is not satisfactory the rigid transformations are updated in block 518.

Figure 6:
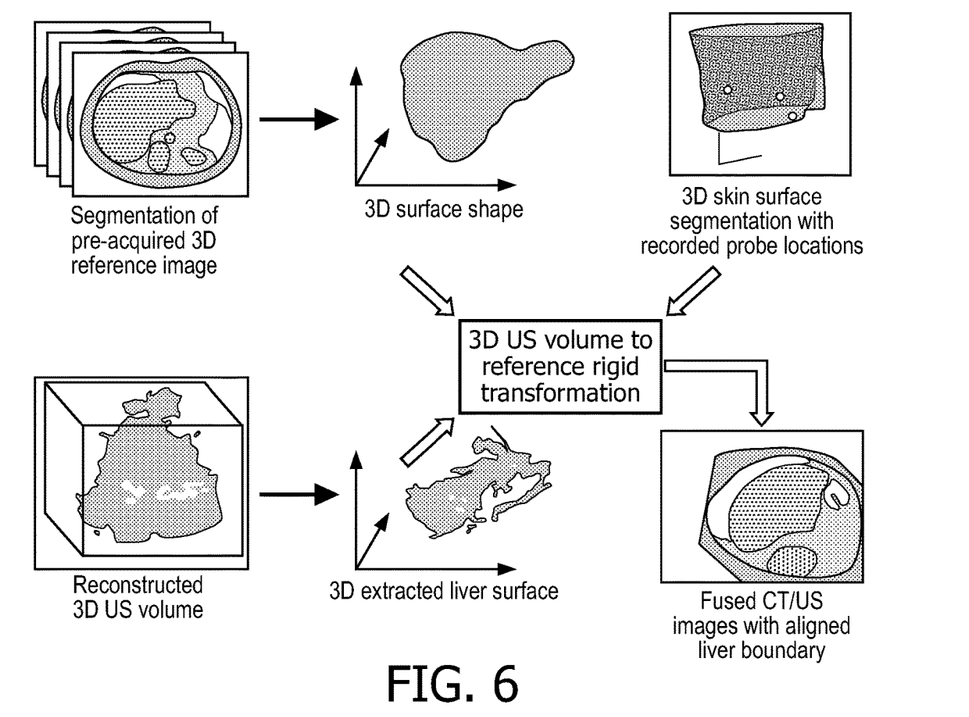
FIG. 6 is a schematic diagram showing images employed in registration processes in accordance with an illustrative embodiment.

Referring to FIG. 6, an illustrative workflow shows image data collection and processing using a CT scan for pre-operative image collection and ultrasonic image collection for real-time (intra-operative) image data. The storage and processing of image data is preferably performed in software running on a workstation (e.g., 112 in FIG. 1) and communicating with external hardware (tracking system, ultrasound scanner, etc.) using real-time electronic data transfer for running a custom-designed clinical workflow.

Prior to the interventional procedure, a 3D volume is obtained in block 702 by using an imaging modality with 3D imaging ability (e.g., MR, CT, etc.). An integrated software tool (e.g., segmentation module 140 and/or processing module 134) is used to perform an automatic and unsupervised segmentation to get a 3D shape of the liver in the pre-operative 3D volume in block 704, as well as a segmentation of the skin surface in block 706.

During the procedure, the patient for an image guided procedure (interventional, diagnostic, etc.) will be positioned on an examination table. A position sensor will be attached to an ultrasound probe. The transmitter/receiver of a tracking system will be positioned close to the patient such that the ultrasound probe with attached position sensor is in the field of view of the transmitter/receiver during the necessary ultrasound imaging for the procedure. The probe is placed at first position perpendicular to the sternum, followed by a second caudal position. A 2D US sweep scan covering the liver will be acquired to reconstruct a 3D ultrasound volume in block 708. The volume and corresponding probe position data will be transferred to the navigation workstation (112). Note that the probe positions may be indicated in the skin segmentation in block 706. In block 710, a liver surface may be extracted from the reconstructed 3D US volume of block 708.

Registration between the pre-acquired 3D volume in block 702 and a segmented 3D reconstructed ultrasound volume in block 708 will be initialized using the information from the probe's tracking data oriented at particular scan planes, then refined using an image-based approach. The real-time 2D ultrasound tissue images and corresponding probe position data will be continuously transferred (streamed) to the workstation (112). Based on a current probe position, the location of the current image relative to the pre-acquired 3D volume of block 702 will be computed using a rigid transformation to align liver (or other organ boundaries) in block 712. On the display 118 of workstation 112, the transformed corresponding intersection contour will be overlaid on the current image to start automatic image segmentation. Fused registered images with aligned liver boundaries are output in block 714.

An ultrasound probe can be tracked using a tracking system such as an electromagnetic system. A position sensor compatible with the tracking system is attached to the ultrasound probe. A one-time calibration procedure is executed to determine the transformation $T_{calibration}$ between a tracking sensor coordinate system and a real-time 2D ultrasound image coordinate system. The pose information $T_{tracking}$ from the tracking sensor is continuously acquired by a workstation.

Prior to the image-guided procedure, the pre-operative image (702) is automatically segmented to obtain a 3D shape model of the liver (704). The shape model $S_{3Dpre}$ is represented by a triangulated mesh with 3D point locations represented in the pre-operative image space coordinate system to have a correspondence to the target image volume. The same pre-operative image is then processed to extract a skin surface $S_{3Dskin}$ by creating a binary volume (706) using a region growing method with a predefined range of values. The binary volume is then filtered to obtain voxels whose neighbors are background voxels.

The 3D US volume (708) can be generated by tracking a 2D probe, streaming to the workstation all 2D image frames and corresponding tracking data, obtaining a "sweep" over the liver area after, e.g., contrast injection, and reconstructing the 3D volume based on the acquired 2D images and tracking data. The reconstructed 3D US volume will be stored on the workstation along with the corresponding transformation $T_{TrackingSystem \rightarrow 3DUS}$ from tracking system coordinates to the reconstructed 3D US voxel coordinates.

The 3D US volume (708) which was reconstructed from the liver organ is then processed to extract a surface (710) to be matched with the pre-acquired liver segmentation. A basic thresholding step is first applied to eliminate zero-valued pixels as well as pixels which are located at, e.g., a 5 cm distance to discard information which may be prone to high tissue deformation. A seed is then automatically determined by selecting the highest valued-pixel at a maximal distance from the US probe, located along the principal axis which was computed by a principal component analysis (PCA) of the US frames. A confidence-based region growing method may be employed and initialized from this seed and iteratively propagated until the binary segmented region converges (i.e., avoids segmentation leakage inside the hepatic tissue and maximized surface extent). A rasterization process is then applied by selecting only the pixels which first intersect an array of rays which originate from the US probe location and directed towards every binary voxel. This creates a mesh surface $S_{3Dintra}$ whose 3D coordinates represent the liver boundary.

Figure 7:
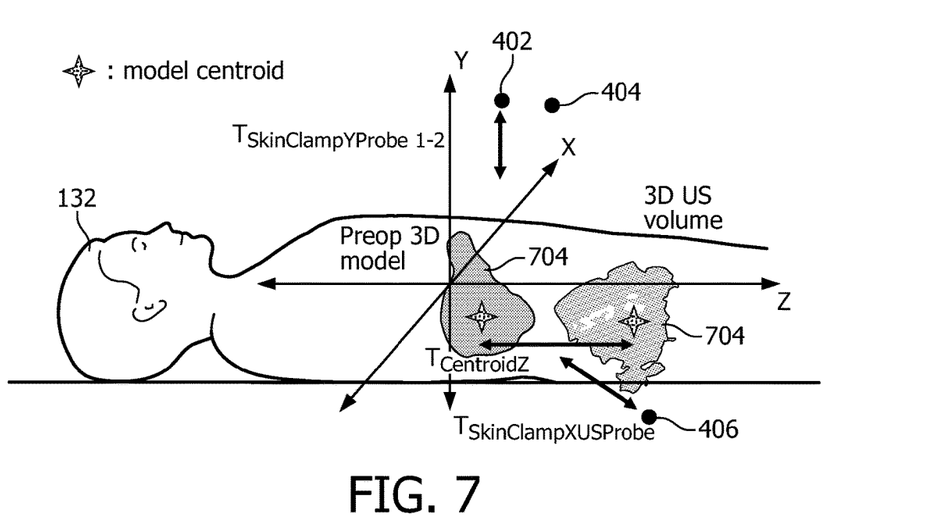
FIG. 7 is a schematic diagram illustratively showing coordinate system adjustment in accordance with one illustrative embodiment.

In block 712, an initial rigid transformation matrix $T_{Init\_3DUS \rightarrow 3DPreop}$ which registers the 3D US volume (708) (or extracted volume (710)) to the 3D pre-operative volume (702) (or 3D model (704)), as depicted in FIG. 7, is initialized with values obtained by the following chain of transformations.

In FIG. 7, the chain of transformations includes: $T_{Init\_3DUS \rightarrow 3DPreop} = T_{SkinClampXUSProbe} \cdot T_{SkinClampYProbe1-2} \cdot T_{CentroidZ} \cdot (T_{ProbePos1})^{-1}$ which first corrects the orientation by computing the inverse of an orientation matrix of $T_{ProbePos1}$, representing the tracking sensor data acquired at a first probe position near a midline. Estimation of the translation parameters in the X, Y, Z axes are determined in the following order:

$T_{CentroidZ}$: translation in the Z axis so to align centroids in the caudal-cranial direction of the pre-operative volume and of the US liver sweep.

$T_{SkinClampYProbe1-2}$: corrects displacement in posterior-anterior direction (Y axis) by translating in the Y direction so that both probe positions (1 and 2) intersect the skin segmentation.

$T_{SkinClampXUSProbe}$: left-right displacement by translating in the X axis the US probe position obtained during the sweep so that it intersects the skin segmentation.

The transformation between the coordinates of reconstructed 3D US volume and pre-acquired 3D reference volume can be computed by using an image-based registration, which may be denoted by $T_{3DUS \rightarrow 3DPreop}$, initialized by the previously defined $T_{Init\_3DUS \rightarrow 3DPreop}$. An illustrative cost function which we seek to minimize to optimize the parameters of $T_{3DUS \rightarrow 3DPreop}$, namely t and R which are the translation and rotation parameters respectively, follows a constrained Iterative Closest Point (ICP)-like objective function which penalizes potential transformation candidates which map probe positions further away from a skin surface:

$$T_{3DUS \rightarrow 3DPreop} = \operatorname*{argmin}_{T} \sum_{i \in S_{3DUS}} [(Rp_i + t - q_i) \cdot n_i]^2 + \sum_{j \in R_{3DCT}} \Psi(R_j^{CT}, R_j^{US}) + \phi(T, b_{1,2,US} S_{3Dskin}).$$

The registration function implements an image similarity metric. The first term is a point-based similarity measure where for each point vertex $q_i$ included in $S_{3DUS}$ of the US mesh, the closest point in the fixed mesh model (from CT) based on a Euclidian distance, is determined and pondered with $n_i$ defined as the normal at each point coordinate of the pre-operative 3D model. These distances are summed for all subsampled mesh vertices from the US surface to maximize the alignment between both segmented point sets. We then incorporate regional salient statistics as a second data related similarity term $\Psi$, which seeks to align corresponding sub-regions of the mesh surfaces. The target CT mesh surface is initially subdivided into smaller regions integrating the following measures: 1) variance of point vertices, 2) cross-correlation between subsets; 3) similarity in curvature. Therefore, we formulate the similarity term as:

$$\Psi(R_j^{CT}, R_j^{US}) = |\sigma_{CTj}^2 - \sigma_{USj}^2| + CC(R_j^{CT}, R_j^{US}) + \|\kappa_{CTj} - \kappa_{USj}\|$$

where $\sigma$ is the standard deviation and $\kappa$ is the variance.

Given an updated transformed US mesh surface, these same statistics are computed in the pre-defined regions with the corresponding mesh region. Finally, a cost assigning function $\Phi$ is linked to the transformation applied to the midline and US sweep probe locations. The former is a Heaviside function which prohibits locations $b_{1,2}$ obtained from the 2 probe locations acquired near the sternum to be mapped further than a 1 cm from the skin such that:

$$H(dist2skin) = \begin{cases} 0, & dist2skin < -10 \\ 100, & dist2skin \geq -10 \end{cases}$$

For the probe location obtained at the sweep, an inversely linear function which allows the mapped location $b_{US}$ to be located between skin and liver surface to allow probe pressure during the image acquisition. First, we detect if the new probe position is outside the skin surface, then the linear Euclidean distance with an added penalizing term (+10) is assigned to the cost, while if $b_{US}$ is inside the CT liver mesh, a higher penalizing cost (+100) is assigned given the improbable scenario. If the probe position lies in between the skin and liver surface, we account for possible probe pressure by calculating the log distance to the closest point of the skin surface such that $\Phi = \log(\|b_{US} - S_{CT\text{-}Skin}\|)$. The closer to the skin, the more probable the solution is. In sum, the cost function can be formulated as:

$$\Phi(b_{US}) = \begin{cases} 10, & \text{if } b_{US} < S_{CT-skin} \\ 100, & \text{if } b_{US} > S_{CT-liver} \\ \log(\|b_{US} - S_{CT-skin}\|), & \text{if } S_{CT-skin} < b_{US} < S_{CT-liver} \end{cases}$$

The first step to optimize the image alignment is a coarse and exhaustive translational search which is first performed to refine the displacement parameters in a group-like fashion. Here the transformation parameters are represented by a quaternion vector and converted to a 4×4 transformation matrix which is applied to the moving points. Once a minimum is obtained, a group-like exhaustive search of rotational parameters is then performed where rotation about the X, Y and Z axes. What is important in this case is that the center of rotation for the transformation is the probe position. Hence, all transformations are applied with regards to the probe's location in space and with respect to liver and skin surface. Therefore when optimizing the rotation parameters, the probe's location remains in the same location.

We perform interpolation of 3D rotation in the quaternion domain, by converting the 3×3 rotational matrices into quaternion. Once the crude refinement is obtained, the 6 degrees of freedom (DOF) are simultaneously optimized using a gradient-descent, non-linear Levenberg-Marquardt optimization scheme. This obtains the minima of the cost function and determines the optimal solution using the starting point provided by the coarse exhaustive search. Other optimizations may also be employed.

Once the registration between the reconstructed 3D US volume 708 and the 3D pre-operative volume 702 is determined after optimization, the position of the current 2D ultrasound frame within the pre-acquired reference image can be determined based on the current tracking data $T_{tracking}$ from the tracking sensor by using the transformation:

$$T_{2DUS \to 3DPreop} = T_{3DUS \to 3DPreop}$$

$$T_{TrackingSystem \to 3DUS} \, T_{ProbeSensor \to TrackingSystem} \, T_{2DUS \to ProbeSensor} =$$

$$T_{3DUS \to 3DPreop} \, (T_{3DUS})^{-1} \, T_{tracking} (T_{calibration})^{-1}$$

where:

$T_{2DUS \to 3DPreop}$ is the transformation from the 2D US image coordinate system to the pre-operative 3D image coordinate system, $T_{2DUS \to ProbeSensor}$ is the transformation from the 2D US image coordinate system to the probe sensor coordinate system (which is the inverse of the so-called calibration transformation $T_{calibration}$), $T_{ProbeSensor \to TrackingSystem}$ is the transformation from the probe sensor coordinate system to the tracking system coordinate system, i.e., the "tracking transformation" $T_{tracking}$ of the ultrasound probe, $T_{TrackingSystem \to 3DUS}$ is an arbitrary "convenience" transformation that positions the reconstructed 3D US volume in tracking system space (and which is by definition the inverse of $T_{3DUS}$).

The workstation (112) will use this relationship to extract, in real-time, an initialization contour, i.e., the intersected 3D surface shape on 2D ultrasound plane that corresponds to the current pose of the 2D tissue image. The contour will be used to start tissue segmentation in this 2D ultrasound image.

It should be understood that the present principles may include other tracking systems. For example, instead of an electromagnetic tracking system, tracking systems based on other physical principles can be employed, such as, optical tracking systems. An alternative embodiment may employ a 3D capable US transducer which permits the acquisition of matrix-based volumetric image data at a single probe location. This may avoid the need of manually sweeping the 2D probe. This may also avoid volume reconstruction errors which can be prone to interpolation and motion artifacts.

In some embodiments, instead of using a single sequence of US images to create a single 3D US volume, a stitching or compounding of multiple image acquisitions may be employed to create a panoramic view representation of the liver or other organ for increased accuracy of the 3D surface segmentation.

In addition, non-rigid image deformation may be accounted for. The assumption of optimizing a rigid transformation between the pre-operative shape model and the intra-operative US data remains valid and accurate if the patient's internal organs do not deform by motion or breathing artifacts. However, this cannot always be assumed as a constant parameter. To enhance the accuracy in the presence of tissue motion, image-based motion correction may be applied to the images to account for deformations.

The present principles may be applied in a variety of clinical procedures in computer aided diagnosis, minimally invasive surgery, interventional radiology, etc. In particular, by using segmented contours for registration, positioning and guidance, the present embodiments can assist in improving ultrasound-based image guidance of diagnostic and therapeutic medical procedures.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for systems and methods for automated initialization and registration of a navigation system (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A method for image registration, comprising:
 tracking a scanner probe in at least one position along a skin surface of a patient;
 acquiring image planes corresponding to the at least one position by an imaging device;
 reconstructing a three-dimensional volume of a region of interest from the image planes by an image processing module;
 initializing a search of an image volume by the image processing module to determine candidate images to register the image volume with the three-dimensional volume by employing pose information of the scanner probe during image plane acquisition, and physical constraints of a pose of the scanner probe in relation to the patient that are necessary for the scanner probe to perform the image plane acquisition; and registering the image volume with the three-dimensional volume by a registration module.

2. The method as recited in claim 1, wherein tracking a scanner probe in at least one position along a skin surface of a patient includes tracking an ultrasonic scanner probe held substantially perpendicular to the skin surface.

3. The method as recited in claim 1, wherein acquiring image planes corresponding to the at least one position includes acquiring image planes at two positions along a midline of a sternum of the patient.

4. The method as recited in claim 1, wherein the area of interest includes an organ.

5. The method as recited in claim 1, wherein reconstructing a three-dimensional volume of a region of interest from the image planes includes acquiring image planes of the area of interest to capture boundaries in the area of interest.

6. The method as recited in claim 5, wherein registering includes aligning the boundaries in the area of interest of the three-dimensional volume with corresponding boundaries of a segmented image volume.

7. The method as recited in claim 1, wherein initializing a search of an image volume includes constraining a search space for the search by employing a patient positioning and the pose of the scanner probe.

8. The method as recited in claim 1, further comprising optimizing alignment between the image volume and the three-dimensional volume by selecting a similarity measure and computing the similarity measure between images.

9. The method as recited in claim 1, further comprising fusing the image volume with the three-dimensional volume.

10. A system for image registration, comprising:
a spatial trackable scanner probe;
an imaging device configured to acquire image planes of a subject corresponding to at least one position of the scanner probe;
an image processing module configured to reconstruct a three-dimensional volume of a region of interest from the image planes, the image processing module further configured to initialize a search of a stored model of the image volume to determine candidate images to register the image volume with the three-dimensional volume by employing pose information of the scanner probe during image plane acquisition, and physical constraints of the pose of the scanner probe in relation to the subject that are necessary for the scanner probe to perform the image plane acquisition; and
a registration module configured to register the image volume with the three-dimensional volume.

11. The system as recited in claim 10, wherein the scanner probe includes an ultrasonic scanner probe tracked with a tracking sensor.

12. The system as recited in claim 10, wherein scanner probe includes an ultrasonic scanner probe which acquires three-dimensional images.

13. The system as recited in claim 12, wherein the area of interest includes an organ.

14. The system as recited in claim 10, wherein organ boundaries in the three-dimensional volume are aligned with corresponding organ boundaries of a segmented image volume.

15. The system as recited in claim 10, wherein the image processing module constrains a search space for the search by employing a patient positioning and the pose of the scanner probe.

16. The system as recited in claim 10, wherein the image processing module optimizes alignment between the image volume and the three-dimensional volume by computing a similarity measure between images.

17. The system as recited in claim 10, wherein the scanner probe includes an orientation measure to define an orientation of the scanner probe to enable use of a single position of acquiring an image plane.

* * * * *